United States Patent [19]
Jameson et al.

[11] Patent Number: 5,645,837
[45] Date of Patent: Jul. 8, 1997

[54] PEPTIDES THAT INHIBIT T CELL ACTIVATION AND METHODS OF USING THE SAME

[75] Inventors: Bradford A. Jameson, Philadelphia; Swati Choksi, Broomall, both of Pa.; Robert Korngold, Cherry Hill, N.J.

[73] Assignee: Thomas Jefferson University, Philadelphia, Pa.

[21] Appl. No.: 372,952

[22] Filed: Jan. 17, 1995

[51] Int. Cl.$^6$ .............................. A61K 38/12; C07K 5/12
[52] U.S. Cl. ..................... 424/185.1; 424/194.1; 530/300; 530/330; 530/324
[58] Field of Search ........................... 530/300, 350, 530/395, 402–403, 868, 324–330; 424/185.1, 193.1, 278.1, 194.1; 514/12–18

[56] References Cited

PUBLICATIONS

Casabo, Lucia G. et al., "T Cell Activation Results in Physical Modification of the Mouse CD8β Chain" *J. of Immuno.* 152:397–404 (1994).
Connolly, Janet M. et al., "Recognition by CD8 on Cytotoxic T Lymphocytes is Ablated by Several Substitutions in the Class I α3 Domain: CD8 and the T–Cell Receptor Recognize the Same Class I Molecule" *PNAS* 87:2137–2141 (1990).
Eichmann, Klaus et al., "Affinity Enhancement and Transmembrane Signalling are Associated with Distinct Epitopes on the CD8 αβ Heterodimer" *J. of Immuno.* 147:2075–2081 (1991).
Franco, Marie–Dominique et al, "Regions of the CD8 Molecule Involved in the Regulation of CD2–Mediated Activation" *Cellular Immuno.* 157:341–352 (1994).
Gallagher, Pauline F. et al., "CD4 and CD8 Molecules can Physically Associate with the Same T–Cell Receptor" *PNAS* 86:10044–10048 (1989).
Giblin, Patricia et al., "A Secreted Form of the Human Lymphocyte Cell Surface Molecule CD8 Arises from Alternative Splicing" *PNAS* 86:998–1002 (1989).
Korngold, R., "Biology of Graft–vs.–Host Disease" *Amer. J. Ped. Hematol. & Oncol.* 15:18–27 (1993).
Leahy, Daniel J. et al., "Crystal Structure of a Soluble Form of the Human T Cell Coreceptor CD8 at 2.6 Å Resolution" *Cell* 68:1145–1162 (1992).
Ledbetter, Jeffrey A. et al., "Lyt–2 and Lyt–3 Antigens are on Two different Polypeptide Subunits Linked by Disulfide Bonds" *J. of Exp. Med.* 153:1503–1516 (1981).
Littman, Dan R. et al., "The Isolation and Sequence of the Gene Encoding T8: A Molecule Defining Functional Classes of T Lymphocytes" *Cell* 40:237–246 (1985).
Merrifield, R.B., "Solid Phase Peptide Synthesis. I. The Synthesis of a Tetrapeptide", *J. Am. Chem. Soc.*, 1963, 85, 2149–2154.
Miceli, M. Carrie and Parnes, Jane R., "Role of CD4 and CD8 in T Cell Activation and Differentiation" *Adv. In Immuno.* 53:59–72 (1993).

Nakauchi, Hiromitsu et al., "Molecular Cloning of Lyt–3, a Membrane Glycoprotein Marking a Subset of Mouse T Lymphocytes: Molecular Homology to Immunoglobulin and T–Cell Receptor Variable and Joining Regions" *PNAS* 84:4210–4214 (1987).
Nakauchi, H. et al, "Molecular Cloning of Lyt–2, a Membrane Glycoprotein Marking a Subset of Mouse T Lymphocytes: Molecular Homology to its Human Counterpart, Leu–2/T8, and to Immunoglobulin Variable Regions" *PNAS* 82:5126–5130 (1985).
Sanders, S.K. et al., "Mutations in CD8 that Affect Interactions with HLA Class I and Monoclonal Anti–CD8 Antibodies" *J. of Exp. Med.* 174:371–379 (1991).
Sukhatme, Vikas P. et al., "The T Cell Differentiation Antigen Leu–2/T8 is Homologous to Immunoglobulin and T Cell Receptor Variable Regions" *Cell* 40:591–597 (1985).
Wheeler, Christopher, J. et al., "An Immunological Role for the CD8 β–Chain" *Nature* 357:247–249 (1992).
Zamoyska, Rose et al., "Two Lyt–2 Polypeptides Arise from a Single Gene by Alternative Splicing Patterns of mRNA" *Cell* 43:153–163 (1985).
Zamoyska, Rose et al., "Inability of CD8α' Polypeptides to Associate with p56$^{lck}$ Correlates with Impaired Function in Vitro and Lack of Expression in Vivo" *Nature* .
Bowie, J. U. et al., Science 247:1306–1310 (1990), "Deciphering the message in protein sequences: tolerance to amino acid substitutions".
B. A. Jameson et al., Nature 369:744–746 (1994), "A rationally designed CD4 analogue inhibits experimental allergic encephalomyelitis".
S. Ponger, Methods in Enzymology 154: 450–473 (1987), "The use of structural profiles and parametric sequence comparison in the rational design of polypeptides".

*Primary Examiner*—Thomas M. Cunningham
*Attorney, Agent, or Firm*—Woodcock Washburn Kurtz Mackiewicz & Norris

[57] ABSTRACT

Compounds that inhibit CD8 mediated T cell activation and that have a molecular surface that corresponds to the molecular surface of human CD8 at amino acids 53–56 and/or 60–67 and pharmaceutical compositions comprising such compounds are disclosed. Method of inhibiting activation of a human T cell are disclosed. The methods comprise contacting a T cell with a compound that inhibits CD8 mediated T cell activation and that has a molecular surface that corresponds to the molecular surface of human CD8 at amino acids 53–56 and/or 60–67. Methods of treating an individual suspected of suffering from or susceptible to graft versus host disease and/or organ rejection are disclosed. The methods comprise administering an effective amount of a compound that inhibits CD8 mediated T cell activation and that has a molecular surface that corresponds to the molecular surface of human CD8 at amino acids 53–56 and/or 60–67.

18 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 114 amino acids
( B ) TYPE: amino acid
( D ) TOPOLOGY: linear ( i i ) MOLECULE TYPE: protein ( x i ) SEQUENCE DESCRIPTION: SEQ ID NO:1:

```
Ser Gln Phe Arg Val Ser Pro Leu Asp Arg Thr Trp Asn Leu Gly Glu
 1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala
```

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Ser Gln Asn Lys
1
```

( 2 ) INFORMATION FOR SEQ ID NO:3:

( i ) SEQUENCE CHARACTERISTICS:
( A ) LENGTH: 8 amino acids
( B ) TYPE: amino acid
( D ) TOPOLOGY: linear ( i i ) MOLECULE TYPE: protein ( x i ) SEQUENCE DESCRIPTION: SEQ ID NO:3:

```
Ala Glu Gly Leu Asp Thr Gln Arg
```

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:4:

```
Cys Ser Gln Asn Lys Cys
1               5
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:5:

```
Cys Ser Gln Asn Lys Pro Cys
1               5
```

(2) INFORMATION FOR SEQ ID NO:6:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:6:

```
Cys Ala Glu Gly Leu Asp Thr Gln Arg Cys
1               5                   10
```

(2) INFORMATION FOR SEQ ID NO:7:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:7:

```
Cys Ser Ser His Asn Lys Pro Cys
1               5
```

(2) INFORMATION FOR SEQ ID NO:8:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:8:

```
Cys Asp Glu Lys Leu Asn Ser Ser Lys Leu Cys
1               5                   10
```

PEPTIDES THAT INHIBIT T CELL ACTIVATION AND METHODS OF USING THE SAME

FIELD OF THE INVENTION

The present invention relates to molecules which interfere with CD8-mediated activity.

BACKGROUND OF THE INVENTION

Clinical allogenic bone marrow transplantation is an important therapeutic treatment for several diseases including high risk leukemia, aplastic anemia, and severe combined immunodeficiency. In addition, there is a wide range of metabolic and genetic disorders that can potentially be corrected by this approach. However, the usefulness of marrow transplantation is currently limited by several important risk factors, the principal one being graft-versus-host disease (GVHD), an often times lethal complication which occurs in a high proportion of transplants (see Korngold, R., Amer. J. Ped. Hematol. & Oncol. 15:18 (1993)).

The risk of GVHD can be reduced by HLA matching of the marrow donor and recipient, with a matched sibling being the primary choice. Yet, less than 30% of the patients in North America have an HLA-matched sibling, and therefore must seek suitable unrelated HLA-matched donors from the National Marrow Donor Program. The probability of finding an unrelated HLA-matched donor is currently on the order of 30–40% and depend on the total number of donors registered. In both related and unrelated HLA-matched transplant situations, the risk of GVHD is still quite high due to disparity of non-HLA multiple minor histocompatibility (H) antigens. GVHD is somewhat higher in unrelated cases, as this increases the probability of differences at these loci.

Mature donor T cells contaminating the marrow inoculum are responsible for GVHD. Several studies have shown that depletion of these T cells significantly diminishes the incidence of disease. However, the elimination of donor T cells has also resulted in a greater incidence of leukemic relapse. It seems important to provide at least some level of T cell immunocompetency in these completely immunocompromised patients to not only combat residual leukemia cells but also to counter opportunistic infections. In this respect, the same GVHD-reactive donor T cells may be important for targeting leukemia cells expressing the same host allogeneic histocompatibility antigens. Therapeutic approaches that could ameliorate the pathogenic tissue destruction accompanying GVHD, particularly in the gut and skin, but that would allow for continued anti-leukemia activity would greatly benefit marrow transplant patients.

Other transplantation procedures involving the implantation of immunogenic tissue include but are not limited to, heart transplants, liver transplants, kidney transplants, lung transplants, islet transplants, cornea transplants and skin grafts. In such procedures, organ rejection is an obstacle to complete recovery. The individual's immune system recognizes antigens (HLA or minor H antigens) on the implanted tissue as foreign and mounts an immune response against it which injures and destroys the implanted tissue.

T cells act as effectors of the immune response. One of the most striking ways in which they do so is by targeting cells displaying foreign antigen. The subset of T cells that mediate this lytic function are designated as cytotoxic T lymphocytes (CTL). The highly specific nature of the CTL response is apparent in cell-mediated responses to vital infections and to allografts. This sub-population of lymphocytes is characterized by expression of the cell surface marker CD8. The CD8 protein has been shown to play a major role in both activation of mature T-cells and the thymic differentiation process that leads to expression of CD8. Classically, CD8 has been viewed as an accessory molecule involved in ligation of class I major histocompatibility complex (MHC) bearing antigen on an antigen presenting cell (APC). In recent years, accumulating evidence suggests that this model for the role of CD8 in T cell activation is not complete. It is now believed that CD8 plays a major role in signal pathways leading to T cell proliferation (for review, see Miceli and Parnes, Adv. In Immuno. 53:59–72 (1993)).

CD8 has been shown to physically associate with the T cell receptor complex (TCR), as demonstrated by co-immunoprecipitation and by co-capping experiments (Gallagher et al., PNAS 86:10044–10048 (1989)). TCR signalling and TCR mediated lymphokine production are markedly enhanced with CD8-TCR aggregation. Characterization of the CD8 structure by a panel of monoclonal antibodies directed against CD8 showed that MHC class I binding and TCR interaction are associated with distinct regions of the CD8 molecule (Eichmann et al., J. of Immuno. 147:2075–2081 (1991). In addition, CD8 and the TCR recognize the same class I molecule (Connoly et al., PNAS 87:2137–2141 (1990)).

The human CD8 molecule is expressed either as an $\alpha/\alpha$ homodimer or as an $\alpha/\beta$ heterodimer. Individual human peripheral T-cells can express varying amounts of CD8 $\alpha/\alpha$ and $\alpha/\beta$ complexes, and their relative ratios appear to be differentially regulated upon T-cell activation. The biological activity of CD8 has primarily been attributed to the $\alpha$ chain, which enhances or reconstitutes T-cell responses in the homodimeric form. In contrast, until recently, no role had been ascribed to the $\beta$ chain. Mice that were chimeric for the homozygous disruption of the CD8 $\beta$ gene developed normally to the CD4+ CD8+ stage, but did not efficiently differentiate further, which results in a low number of peripheral CD8+ T-cells. The fact that the number of peripheral CD8+ T-cells was restored upon transfer of exogenous CD8 $\beta$ gene indicates that CD8 $\beta$ is necessary for the maturation of CD8+ T-cells. It has also been shown that CD8 $\alpha/\beta$ transfectants produce more IL-2 than CD8 $\alpha/\alpha$ transfectants in response to specific stimuli (Wheeler et al., Nature 357:247–249 (1992)). T-cell activation results in the physical modification of the mouse CD8 $\beta$ chain shown by the reversible alteration in its sialic acid content (Casabo et al., J. of Immuno. 152:397–404 (1994)). This modification may influence the physical structure of the CD8 complex and in turn the interaction with TCR and MHC class I. The gene encoding the CD8 molecule has been cloned for several species (human, rat, mouse) (Sukhame et al., Cell 40:591–597 (1985); Nakauchi et al, PNAS 82:5126–5130 (1985)). The murine CD8 molecule is expressed as a heterodimeric structure consisting of two disulfide linked subunits; Lyt-2, which has a molecular weight of about 38 kDa and Lyt-3, which has a molecular weight of 30 kDa (Ledbetter et al., J. of Exp. Med. 153:1503–1516 (1981)). The $\alpha$ chain gene can also undergo an alternative mode of mRNA splicing resulting in expression of the $\alpha'$ form which is distinguishable from $\alpha$ by its shorter cytoplasmic tail (Zamoyska et al., Nature 342:278 (1989); Giblin et al., PNAS 86:998–1002 (1989)).

Sequence analysis of CD8 indicates that it is a member of the immunoglobulin (Ig) superfamily. Members of the Ig-superfamily exhibit highly conserved hydrophobic cores. The CD8 molecule consists of an unique amino-terminal Ig-variable domain, an extracellular spacer which carries the structural features of Ig hinge-line region, a transmembrane domain and an intracellular cytoplasmic tail. The crystal structure of the extracellular Ig-like portion of the homodimeric human CD8α has been recently solved [Leahy et al., *Cell* 68:1145–1162 (1992)]. The amino-terminal domain of the CD8α chain was shown to closely resemble an Ig-variable region. The regions that are analogous to antigen-binding domains on an immunoglobulin protein are referred to as the complementarity determining regions (CDRs). Recent mutagenesis studies of the different domains of CD8 has indicated that CDR1 and CDR2 like domains are involved in MHC class I interactions (Sanders et al., *J. of Exp. Med.* 174:371–379 (1991)).

Replacement of the human CD8α CDR2-like loop by the homologous mouse sequences results in the loss of interaction of monoclonal antibodies (MAb) that are capable of inhibiting CD2-mediated $Ca^{+2}$ increases (Franco et al, *Cellular Immuno.* 157:341–352 (1994)). This suggests that the CDR2-like region of CD8 α-chain may be involved in regulating T-cell activation.

These data indicate that the role of CD8 in MHC class I interaction is not incidental, but required for efficient stimulation of the T cell. The CD8 molecule plays a role very similar, yet distinct, to that of CD4 in class II MHC-restricted activation. Thus, CD8 must be involved in the regulation of a complex system of modulation of signalling involving many closely related molecules.

There is a need for pharmaceutical compositions which can effectively inhibit the immune responses mediated by CD8 activity. There is a need for a method of inhibiting CD8 mediated T cell activation. There is a need for pharmaceutical compositions which can effectively inhibit GVHD in individuals undergoing allogeneic bone marrow transplantation and grafting procedures. There is a need for pharmaceutical compositions which can effectively inhibit organ and tissue rejection in individuals undergoing transplantation and grafting procedures.

SUMMARY OF THE INVENTION

The present invention relates to compounds that compete with CD8 in intermolecular interactions that involve CD8 which are associated with CTL activation. The compounds comprise a molecular surface that corresponds to a molecular surface of human CD8 at amino acids 53–56, 60–67, or 53–67. The compound competes with CD8 in intermolecular interactions. By competing with CD8, the compound inhibits CD8 from participating is such intermolecular interactions and thereby inhibits CTL activation. By competing with CD8 but not. activating CTL, the compounds of the invention are CD8 antagonists.

The present invention relates to peptides consisting of a) less than 25 amino acids, and b) an amino acid sequence comprising at least CD8 amino acids 53–56 or CD8 amino acids 60–67 wherein said peptide inhibits CD8 activity.

The present invention relates to pharmaceutical composition comprising:

a) synthetic peptide consisting of
   i) less than 25 amino acids, and
   ii) an amino acid sequence comprising at least CD8 amino acids 53–56 or CD8 amino acids 60–67 wherein said peptide inhibits CD8 activity; and b) a pharmaceutically acceptable carrier or diluent.

The present invention relates to methods of inhibiting human CTL activation comprising contacting human CTL with a compound that competes with CD8 in intermolecular interactions that involve CD8 which are associated with CTL activation. The compound comprises a molecular surface that corresponds to a molecular surface of human CD8 at amino acids 53–56, 60–67, or 53–67. The compound competes with CD8 in intermolecular interactions, thus inhibiting CD8 from participating in such intermolecular interactions and thereby inhibiting CTL activation.

The present invention relates to methods of inhibiting human CTL activation comprising contacting human CTL with a peptide consisting of a) less than 25 amino acids, and b) an amino acid sequence comprising at least CD8 amino acids 53–56 or CD8 amino acids 60–67 wherein said peptide inhibits CD8 activity.

The present invention relates to methods of treating individuals who are about to undergo, are undergoing and/or have undergone transplantation procedures comprising the step of:

administering to an individual an effective amount of a compound that competes with CD8 in intermolecular interactions that involve CD8 which are associated with CTL activation. The compound comprises a molecular surface that corresponds to a molecular surface of human CD8 at amino acids 53–56, 60–67, or 53–67. The compound competes with CD8 in intermolecular interaction, thus inhibiting CD8 from participating is such intermolecular interactions and thereby inhibiting CTL activation.

The present invention relates to methods of treating individuals who are about to undergo, are undergoing and/or have undergone transplantation procedures comprising the step of:

administering to an individual an effective amount of a peptide consisting of
   a) less than 25 amino acids, and
   b) an amino acid sequence comprising at least CD8 amino acids 53–56 or CD8 amino acids 60–67 wherein said peptide inhibits CD8 activity.

DETAILED DESCRIPTION OF THE INVENTION

As used herein, the term "CD8" is meant to refer to human CD8 protein unless otherwise specifically designated as CD8 derived from a different species. The sequence of human CD8 protein is known and is disclosed in Littman et al., *Cell* 40:237–246 (1985). The sequence of the extracellular domain of the α chain of human CD8 is shown in SEQ ID NO: 1. When CD8 amino acids are referred to by CD8 amino acid number, the number is determined from SEQ ID NO: 1. The sequence of murine CD8 protein is known and is disclosed in Zamoyska et al., *Cell* 43:153–163 (1985) and Nakauchi et al., *PNAS* 84: 4210–4214.

The present invention provides compounds that compete with CD8. Specifically, two regions of human CD8 α chain have been identified which interact with other molecules in the mediation of immune responses and the activation of T cells. The compounds of the present invention effectively inhibit the immune responses mediated by CD8 activity. The compounds of the present invention effectively inhibit GVHD in individuals undergoing allogeneic bone marrow transplantation procedures. The compounds of the present invention inhibit CD8 mediated CTL activation. The compounds of the present invention effectively inhibit immune responses associated with organ and/or tissue rejection in individuals undergoing organ and/or tissue transplantation procedures.

The compounds of the present invention are CD8 antagonists. The compounds comprise a molecular surface that is corresponds to the molecular surface of human CD8 α chain at amino acids 53–56, 60–67, or 53–67. However, while the compounds interact with molecules that CD8 interacts with in at the same site that CD8 does by mimicking the surface of human CD8 at amino acids 53–56, 60–67, or 53–67, the interactions by the compounds does not result in CTL activation. Furthermore, the compounds, by competing with CD8, inhibit CTL activation. Thus, the CD8 antagonist compounds compete with native CD8 but do not produce the same biological effect. Accordingly, the CD8 antagonist compounds of the invention are effective inhibitors of CD8.

As used herein, the term "corresponds" is meant to refer to a similarity in structure which is sufficient to result in mimicry of activity. That is, the molecular surface of the compounds of the invention have a surface whose structure interacts with the surface molecules that CD8 interacts with in the same manner. The structure of a molecular surface is the result of amino acid side chains and the forces place upon them by the adjacent groups and the conformation of the backbone. In some embodiments, corresponding surfaces are essentially identical.

The present invention provides compounds that display the same molecular surface as that which is displayed by amino acids 53–56 and/or 60–67 of human CD8. By displaying the same molecular surface as regions of human CD8, the compounds of the present invention interact with the same molecules as CD8 amino acids 53–56 and/or 60–67. The compounds of the present invention do not produce the same biological effect that is produced by CD8 intermolecular interaction.

According to some embodiments of the present invention, portions of the CD8 molecule which include residues 53–56, SEQ ID NO: 2, and/or 60–67, SEQ ID NO: 3, alone or linked to additional CD8 and/or non-CD8 sequences, are included in small peptides and form a surface that participates in intermolecular interactions in competition with native CD8 amino acids 53–56 and 60–67, respectively. The present invention also provides small peptides which have a molecular surface that is substantially similar to the molecular surface formed by CD8 amino acids 53–56 and/or 60–67 in human CD8 but which include one or more conservative substitutions of CD8 residues 53–56 and/or 60–67. When interacting with molecules which interact with CD8, the compounds of the invention do not produce the same biological effect on cells as that which occurs through CD8 interactions. The presence of the compounds of the invention compete with and displace CD8, thereby reducing CD8 mediated immune responses and CTL activation.

The molecular surfaces defined by CD8 amino acids 53–56 or 60–67 are simulated by the compounds of the invention and it is the structural similarity to these surfaces that make the compounds useful in the methods of the present invention. In order for compounds to display substantially the same molecular surface as that which is displayed by CD8 at CD8 amino acids 53–56 or 60–67, compounds include those amino acid sequences in similar conformations as the amino acid sequences occur in the CD8 molecule. In some embodiments of the invention, compounds comprise CD8 amino acids 53–56 in similar conformation as they occur in CD8. In some embodiments of the invention, compounds comprise CD8 amino acids 60–67 in similar conformation as they occur in CD8. Compounds may comprise additional amino acids or molecular entities or moieties provided the active sequence, i.e. CD8 amino acids 53–56 or 60–67, is in an active conformation, i.e. a similar conformation as the sequence that is present in CD8. In some contemplated embodiments, some or all of the amino acids in the active sequence are substituted with conservative substitutions of amino acids.

According to some preferred embodiments, CD8 amino acids 53–56, SEQ ID NO: 2, are used in peptides of the invention. Peptides of some embodiments of the present invention consist of amino acids 53–56 plus amino terminal and carboxy terminal cysteines, SEQ ID NO: 4. The peptide is useful in the treatment of GVHD. The peptide is a conformationally restricted cyclic peptide cyclicized by a disulfide bond formed between the amino terminal and carboxy terminal cysteines. The conformationally restricted peptide will display substantially the same surface as CD8 at amino acids 53–56 but it, SEQ ID NO: 4, will not produce the same biological effect as that which is identified with CD8 intermolecular interactions.

According to some preferred embodiments, CD8 amino acids 53–56, SEQ ID NO: 2, are used in peptides of the invention. Peptides in some embodiments of the invention consist of amino acids 53–56 plus an amino terminal cysteine and a carboxy terminal proline-cysteine to form SEQ ID NO: 5. The peptide is useful in the treatment of GVHD. The peptide is a conformationally restricted cyclic peptide cyclicized by a disulfide bond formed between the amino terminal and carboxy terminal cysteines. The conformationally restricted peptide will display substantially the same surface as CD8 at amino acids 53–56 but it, SEQ ID NO: 5, will not produce the same biological effect as that which is identified with CD8 intermolecular interactions.

According to some preferred embodiments, CD8 amino acids 60–67, SEQ ID NO: 3, are used in peptides of the invention. Peptides that consist of amino acids 60–67 plus amino terminal and carboxy terminal cysteines, SEQ ID NO: 6, are an effective inhibitor of CD8 mediated T cell activation. As such, the peptide is useful in the treatment of GVHD. The peptide is a conformationally restricted cyclic peptide cyclicized by a disulfide bond formed between the amino terminal and carboxy terminal cysteines. The conformationally restricted peptide will display substantially the same surface as CD8 at amino acids 60–67 but it, SEQ ID NO: 6, will not produce the same biological effect as that which is identified with CD8 intermolecular interactions.

The present invention relates to molecules that display the same surface as CD8 at amino acids 53–56 and/or 60–67 and which inhibit CD8 mediated immune responses such as CD8 mediated T cell activation.

The present invention relates to molecules that display the same surface as CD8 at amino acids 53–56 and/or 60–67 and which do not produce the same biological effect as CD8 does when participating in intermolecular interactions. The discovery that molecules that display the same molecular surface as is displayed by CD8 amino acids 53–56 or 60–67 provides the information necessary to create molecules which are effective inhibitors of CD8 mediated immune responses such as CD8 mediated T cell activation. Specifically, molecules of the present invention display the molecular surface that is displayed by CD8 at amino acids 53–56 or 60–67. The remaining portions of the molecules of the present invention are confined to those which do neither impede the molecule from assuming the correct conformation to form the proper molecular surface nor present interfering surfaces which would prevent the molecule from interacting similar to CD8.

According to some embodiments of the present invention, the invention can be represented by the formula:

$R_1-R_2-R_3-R_4-R_5$ wherein:

$R_1$, $R_2$, $R_3$, $R_4$ and $R_5$ taken together are 25 amino acids or less and $R_1$ is a linking moiety, preferably cysteine or penicillamine;

$R_2$ is 0–10 amino acids, preferably 0 amino acids;

$R_3$ is SEQ ID NO: 2, SEQ ID NO: 3 or an amino acid sequence comprising both SEQ ID NO: 2 and SEQ ID NO: 3;

$R_4$ is 0–10 amino acids, preferably 0 amino acids; and $R_5$ is a linking moiety, preferably cysteine or penicillamine.

It is preferred that $R_4$ is 0–1 amino acids. In some embodiments, $R_4$ is proline. It is preferred that $R_4$ is 0 amino acids.

It is preferred that $R_5$ is cysteine or penicillamine. It is more preferred that $R_5$ is cysteine.

In preferred embodiments, the compound is SEQ ID NO: 4, SEQ ID NO: 5 or SEQ ID NO: 6.

In some embodiments, SEQ ID NO: 2 or SEQ ID NO: 3 may contain conservative substitutions.

In some preferred embodiments, peptides have the following formula.

$R_{11}-R_{12}-R_{13}-R_{14}-R_{15}-R_{16}$ wherein:

$R_{11}$ is cysteine or penicillamine;

$R_{12}$ is serine or threonine;

$R_{13}$ is glutamine or asparagine;

$R_{14}$ is asparagine or glutamine;

$R_{15}$ is lysine, hydroxylysine, proline-lysine or proline-hydroxylysine; and, $R_{16}$ is cysteine or penicillamine.

In some preferred embodiments, $R_{11}$ is cysteine. In some preferred embodiments, $R_{12}$ is serine. In some preferred embodiments, $R_{13}$ is glutamine. In some preferred embodiments, $R_{14}$ is asparagine. In some preferred embodiments, $R_{15}$ is lysine or proline-lysine. In some preferred embodiments, $R_{16}$ is cysteine. In some preferred embodiments, $R_{11}$ is cysteine, $R_{12}$ is serine, $R_{13}$ is glutamine, $R_{14}$ is asparagine, $R_{15}$ is lysine and $R_{16}$ is cysteine (SEQ ID NO: 4). In some preferred embodiments, $R_{11}$ is cysteine, $R_{12}$ is serine, $R_{13}$ is glutamine, $R_{14}$ is asparagine, $R_{15}$ is proline-lysine and $R_{16}$ is cysteine (SEQ ID NO: 5).

In some preferred embodiments, peptides have the following formula.

$R_{21}-R_{22}-R_{23}-R_{24}-R_{25}-R_{26}-R_{27}-R_{28}-R_{29}-R_{30}$ wherein:

$R_{21}$ is cysteine or penicillamine;

$R_{22}$ is alanine, valine, isoleucine, leucine or glycine;

$R_{23}$ is glutamic acid or aspartic acid;

$R_{24}$ is glycine, valine, isoleucine, leucine or alanine;

$R_{25}$ is leucine, valine, isoleucine, alanine or glycine;

$R_{26}$ is aspartic acid and glutamic acid;

$R_{27}$ is threonine and serine;

$R_{28}$ is glutamine or asparagine;

$R_{29}$ is arginine; and, $R_{30}$ is cysteine or penicillamine.

In some preferred embodiments, $R_{21}$ is cysteine. In some preferred embodiments, $R_{22}$ is alanine. In some preferred embodiments, $R_{23}$ is glutamic acid. In some preferred embodiments, $R_{24}$ is glycine. In some preferred embodiments, $R_{25}$ is leucine. In some preferred embodiments, $R_{26}$ is aspartic acid. In some preferred embodiments, $R_{27}$ is threonine. In some preferred embodiments, $R_{28}$ is glutamine. In some preferred embodiments, $R_{30}$ is cysteine. In some preferred embodiments, $R_{21}$ is cysteine, $R_{22}$ is alanine, $R_{23}$ is glutamic acid, $R_{24}$ is glycine, $R_{25}$ is leucine, $R_{26}$ is aspartic acid, $R_{27}$ is threonine, $R_{28}$ is glutamine, $R_{29}$ is arginine and $R_{30}$ is cysteine (SEQ ID NO: 6).

Peptides are provided which have 4–25 amino acids, preferably 6–20 amino acids, more preferably 6–10 amino acids. The peptides comprise CD8 amino acids 53–56 and/or 60–67. These peptides have a restricted conformation and the ability to inhibit CD8 mediated immune responses such as CD mediated T cell activation. The inhibition of CD8 mediated immune responses can be used as the mechanism to prevent or reduce the severity of GVHD in individuals who are undergoing or who have undergone allogenic bone marrow transplantation procedures, or to prevent or reduce rejection in individuals who are undergoing or who have undergone organ and/or tissue transplantation.

In order to maximize the overlap between the conformational repertoire of CD8 with that of the peptides of the invention, peptides have been circularized via an artificially introduced disulfide bridge. Amino terminal and carboxy terminal cysteines have been provided which can be used for formation of disulfide bonds which cyclicize the peptide. Similarly, penicillamine may be used at the amino terminal, carboxy terminal or both to provide the necessary group to form disulfide bonds with opposing penicillamine or cysteines. With the restraints which occur when the peptides are cyclicized, the peptides adopt a folding pattern similar to that of the corresponding domain in CD8.

The present invention provides synthetic peptides that are less than 25 amino acids and comprise amino acids 53–56 and/or 60–67 of CD8. The present invention provides synthetic peptides which contain an amino acid sequence from CD8 that includes CD8 amino acids 53–56 or 60–67 or both, and optionally also includes other CD8 amino acids. Non-CD8 amino acid sequences are provided in some embodiments. The peptides are conformationally restricted, and are generally cyclicized. In some embodiments, non-CD8 sequences are included to for the purposes of conformational restriction. In embodiments that comprise both CD8 and non-CD8 sequences, at least 20–25% of the amino acid sequence of the peptides of the present invention are derived from CD8 including CD8 amino acid sequence 53–56 or 60–67. It is preferred that greater than about 20–25% of the amino acid sequence of the peptides of the present invention are derived from CD8, more preferably 30–40% and more preferably greater than 50%. In some embodiments, the percentage of amino acid sequence of the peptides of the present invention derived from CD8 approaches about 60% or about 75% or more.

The peptides of the present invention may be prepared by any of the following known techniques. Conveniently, the peptides may be prepared using the solid-phase synthetic technique initially described in Merrifield (1963) *J. Am. Chem. Soc.* 15:2149–2154. Other peptide synthesis techniques may be found, for example, in M. Bodanszky et al., *Peptide Synthesis*, John Wiley & Sons, 2d Ed. (1976); Kent and Clark-Lewis in *Synthetic Peptides in Biology and Medicine*, p. 295–358, eds. Alitalo, K., Partanen, P. and Vakeri, A., Elsevier Science Publishers, (Amsterdam, 1985); as well as other reference works known to those skilled in the art. A summary of peptide synthesis techniques may be found in J. Stuart and J. D. Young, *Solid Phase Peptide Synthelia*, Pierce Chemical Company, Rockford, Ill. (1984). The synthesis of peptides by solution methods may also be used, as described in *The Proteins*, Vol. II, 3d Ed., p. 105–237, Neurath, H. et al., Eds., Academic Press, New York, N.Y. (1976). Appropriate protective groups for use in such syntheses will be found in the above texts, as well as in J. F. W. McOmie, *Protective Groups in Organic Chemistry*, Plenum Press, New York, N.Y. (1973).

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

The present peptides may also be prepared by recombinant DNA techniques, although such methods are not preferred because of the need for purification and subsequent chemical modifications to conformationally restrain the peptides.

In addition to peptides which comprise L amino acids, pharmaceutical compositions according to the present invention may comprise peptides made up of D amino acids. Because most enzymes involved in degradation recognize a tetrahedral alpha-carbon, the D-amino acids were utilized in order to avoid enzyme recognition and subsequent cleavage. Our computer studies indicate that the same folded presentation of the peptide is accomplished by reversing the amino acid sequence, employing D-amino acids. Thus, peptides comprised of D amino acids are less susceptible to degradation.

Conservative substitutions in the amino acid sequence may be made. Those having ordinary skill in the art can readily design compounds of the invention with conservative substitutions for CD8 amino acids. For example, following what are referred to as Dayhof's rules for amino acid substitution (Dayhof, M. D. (1978) *Nat. Biomed. Res. Found.*, Washington, D.C. Vol. 5, supp. 3), amino acid residues in a peptide sequence may be substituted with comparable amino acid residues. Such substitutions are well known and are based the upon charge and. structural characteristics of each amino acid.

L or D amino acids may be used in the synthesis. Peptides may be synthesized with amino acid sequences in the order they occur in CD8 or in the reverse order. In peptides comprising all L amino acids, it is preferred that they are synthesized such that the amino acid sequences are assembled in the order that they occur in CD8. In peptides comprising all D amino acids, it is preferred that they are synthesized such that the amino acid sequences are assembled in the reverse order that they occur in CD8.

Synthesized peptides may be circularized in order to mimic the geometry of those portions as they occur in CD8. Circularization may be facilitated by disulfide bridges between cysteine residues. Alternatively, the peptides may be circularized by means of covalent bonds, such as amide bonds, between amino acid residues of the peptide such as those at or near the amino and carboxy termini.

Peptides for use in pharmaceutical compositions of the present invention may be designed following the guidelines set out herein and using well known processes. Methods of synthesizing peptides and circularizing them may be performed routinely using standard techniques and readily available starting materials.

The present invention relates to a method of therapeutically or prophylactically treating an individual suffering from or susceptible to graft versus host disease. Such individuals include those who are undergoing and/or who have undergone transplantation procedures such as allogeneic bone marrow transplants. Those having ordinary skill in the art can readily identify individuals suspected of suffering from or being susceptible to graft versus host disease. Those with ordinary skill in the art could readily identify individuals for whom administration of the compounds of the invention would be beneficial to alleviate or prevent immune response associated with GVHD. Treatment may be provided prophylactically in conjunction with transplantation procedure or in response to symptoms associated with GVHD. Pharmaceutical compositions useful in the methods of the present invention comprise the compounds described herein.

The method of therapeutically or prophylactically treating an individual suffering from or susceptible to GVHD comprises administering to such an individual an effective amount of a peptide according to the invention. A prophylactically effective amount is an amount which is effective to prevent or decrease the immune response associated with GVHD in an individual susceptible to GVHD. A therapeutically effective amount is an amount which is effective to decrease or eliminate GVHD in an individual suffering from GVHD. Those having ordinary skill in the art can readily and routinely determine the ranges of both prophylactically and therapeutically effective amounts of the peptides of the invention without undue experimentation.

The present invention relates to methods of therapeutically or prophylactically treating an individual suffering from or susceptible to organ and/or tissue rejection. Such individuals include those who are undergoing and/or who have undergone organ and/or tissue transplant procedures such as, for example, liver transplants, heart transplants, kidney transplants, lung transplants, islets transplants, cornea transplants, bone marrow transplants and skin grafts. Those having ordinary skill in the art can readily identify individuals suspected of suffering from or being susceptible to organ and/or tissue rejection. Those with ordinary skill in the art could readily identify individuals for whom administration of the compounds of the invention would be beneficial to alleviate or prevent immune response associated with organ/tissue rejection. Treatment may be provided prophylactically in conjunction with transplantation procedure or in response to symptoms associated with organ or tissue rejection. Pharmaceutical compositions useful in the methods of the present invention comprise the compounds described herein.

The method of therapeutically or prophylactically treating an individual suffering from or susceptible to organ or tissue rejection comprises administering to such an individual an effective amount of a peptide according to the invention. A prophylactically effective amount is an amount which is effective to prevent or decrease the immune response associated with organ and tissue rejection in an individual susceptible to organ or tissue rejection. A therapeutically effective amount is an amount which is effective to decrease or eliminate organ or tissue rejection in an individual suffering from organ or tissue rejection. Those having ordinary skill in the art can readily and routinely determine the ranges of both prophylactically and therapeutically effective amounts of the peptides of the invention without undue experimentation.

The present invention provides pharmaceutical compositions that comprise the peptides of the invention and pharmaceutically acceptable carriers or diluents. The pharmaceutical composition of the present invention may be formulated by one having ordinary skill in the art. Suitable pharmaceutical carriers are described in *Remington's Pharmaceutical Sciences*, A. Osol, a standard reference text in this field, which is incorporated herein by reference. In carrying out methods of the present invention, conjugated compounds of the present invention can be used alone or in combination with other diagnostic, therapeutic or additional agents. Such additional agents include excipients such as coloring, stabilizing agents, osmotic agents and antibacterial agents.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical. stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. In some embodiments, compounds are administered 1–2 days prior to transplantation, preferably 4–12 hours. Compounds may be delivered during transplantation procedures. In some embodiments, compounds are administered for 2 weeks to 2 months after transplantation procedures.

The pharmaceutical compositions of the present invention may be administered by any means that enables the active agent to reach the targeted cells. These methods include, but are not limited to, oral, topical, intradermal, subcutaneous, intravenous, intramuscular and intraparenteral modes of administration. The compounds may be administered singly or in combination with other compounds. The compounds of the invention are preferably administered with a pharmaceutically acceptable carrier selected on the basis of the selected route of administration and standard pharmaceutical practice.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

EXAMPLES

Example 1

Peptides were designed using sequence information derived from the sequence of the α chain of the CD8 protein. These peptides were synthesized and observed to inhibit the CD8-dependent activation pathways of the CTL. Two "active" loop regions have been identified. In the human CD8 the two loops are centered in and around residues Ash 55-Lys 56 and residues Leu 63-Asp 64. The corresponding murine equivalent loops are located in and around murine residues Ser 55-His 56 and Leu 66-Asn 67, respectively.

The following peptides were synthesized based on the corresponding murine sequences:

1) C-S-S-H-N-K-P-C, SEQ ID NO: 7 (referred to as SC2; including murine sequences 55–59); and
2) C-D-E-K-L-N-S-S-K-L-C, SEQ ID NO: 8 (referred to as SC11 ; murine sequences 63–71). The underlined portion of these sequences refer to the sequences derived from the murine CD8 protein.

The murine peptides parallel the active regions of human peptides. Experiments are performed in murine models to test the pharmacological activity of the murine peptides. These results are comparable to the use of parallel peptides based upon human sequences for the treatment of human conditions.

Example 2. Inhibition of Cytotoxic T-cell Mediated Lympholysis by Peptide

The effect of peptide on cytotoxicity was measured in a 4 hour $^{51}$Cr release assay. H-$2^b$ specific effectors were generated in a AKR/J (H-$2^k$) anti C57BL/6 (H-$2^b$) mixed lymphocyte reaction. The stimulators (C57BL/6 spleen cells) are gamma-irradiated at 1500 RADS. The targets were obtained from a tumor cell line, EL-4 (H-$2^b$), that were labelled with Na$^{51}$CrO$_4$. On Day 5 the effectors are harvested and counted. The peptide, at concentrations of 100 µg/ml, 10 µg/ml or 1 µg/ml, was first incubated for 30 minutes at 37° C. with effectors of varying numbers and then $^{51}$Cr labelled targets were added in a 4 hour specific lysis experiment. The target cell lysis was assessed at Effector: Target ratios of 30:1, 10:1, 3:1, and 1:1. Toxic effects of the peptide was determined by the % specific lysis above background that was obtained by incubating just peptide and labelled targets. No toxic effects were observed. Also, anti-CD8 monoclonal antibody that blocks the interaction resulting in lowered lympholysis is used in the assay. SC2 inhibits specific lysis of targets in a concentration dependent manner and SC11 does not.

Example 3. Inhibition of Activation/Generation of Cytotoxic T-cells by Peptide The effect of the peptide on the activation of CTL capable of lympholysis was determined by generating effector T-cells in AKR/J anti C57BL/6 mixed lymphocyte reaction in the presence of peptide. On Day-6, effectors are washed and then $^{51}$Cr-labelled EL-4 targets were added in a 4-hour specific lysis experiment. Both SC2 and SC11 show inhibition of specific lysis of targets in a concentration dependent manner indicating that they may be preventing the induction of activated CTL.

We claim:

1. A conformationally restricted peptide consisting of 4 to 25 amino acids including SEQ ID NO: 2, wherein said peptide inhibits CD8 mediated T cell activation.

2. The conformationally restricted peptide of claim 1 having the formula:

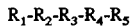

wherein:
- $R_1$ is a linking moiety;
- $R_2$ is 0–10 amino acids;
- $R_3$ is SEQ ID NO: 2;
- $R_4$ is 0–10 amino acids; and
- $R_5$ is a linking moiety.

3. The conformationally restricted peptide of claim 1 having the formula:

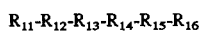

wherein:
- $R_{11}$ is cysteine or penicillamine;
- $R_{12}$ is serine;
- $R_{13}$ is glutamine;
- $R_{14}$ is asparagine;
- $R_{15}$ is lysine; and,
- $R_{16}$ is cysteine or penicillamine.

4. The conformationally restricted peptide of claim 3 wherein said conformationally restricted peptide consists of SEQ ID NO: 4.

5. A pharmaceutical composition comprising:
a) a conformationally restricted peptide of claim 2 and
b) a pharmaceutically acceptable carrier or diluent.

6. The pharmaceutical composition of claim 5 wherein said conformationally restricted peptide has the formula:

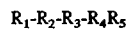

wherein:
- $R_1$ is a linking moiety;
- $R_2$ is 0–10 amino acids;
- $R_3$ is SEQ ID NO:2;
- $R_4$ is 0–10 amino acids; and
- $R_5$ is a linking moiety.

7. The pharmaceutical composition of claim 5 wherein said conformationally restricted peptide has the formula:

wherein:
- $R_{11}$ is cysteine or penicillamine;
- $R_{12}$ is serine;
- $R_{13}$ is glutamine;
- $R_{14}$ is asparagine;
- $R_{15}$ is lysine; and,
- $R_{16}$ is cysteine or penicillamine.

8. The pharmaceutical composition of claim 7 wherein said conformationally restricted peptide consists of SEQ ID NO: 4.

9. A method of inhibiting activation of a human T cell comprising contacting said cell with a peptide of claim 1.

10. The method of claim 9 wherein said conformationally restricted peptide has the formula:

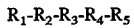

wherein:
- $R_1$ is a linking moiety;
- $R_2$ is 0–10 amino acids;
- $R_3$ is SEQ ID NO: 2;
- $R_4$ is 0–10 amino acids; and
- $R_5$ is a linking moiety.

11. The method of claim 9 wherein said conformationally restricted peptide has the formula:

wherein:
- $R_{11}$ is cysteine or penicillamine;
- $R_{12}$ is serine;
- $R_{13}$ is glutamine;
- $R_{14}$ is asparagine;
- $R_{15}$ is lysine; and,
- $R_{16}$ is cysteine or penicillamine.

12. The method of claim 11 wherein said conformationally restricted peptide consists of SEQ ID NO:4.

13. A method of treating an individual who is about to undergo, is undergoing and/or has undergone transplantation procedures comprising the step:
administering an effective amount of a peptide of claim 1.

14. The method of claim 13 wherein said conformationally restricted peptide has the formula:

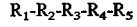

wherein:
- $R_1$ is a linking moiety;
- $R_2$ is 0–10 amino acids;
- $R_3$ is SEQ ID NO:2;
- $R_4$ is 0–10 amino acids; and
- $R_5$ is a linking moiety.

15. The method of claim 13 wherein said conformationally restricted peptide has the formula:

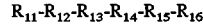

wherein:
- $R_{11}$ is cysteine or penicillamine;
- $R_{12}$ is serine;
- $R_{13}$ is glutamine;
- $R_{14}$ is asparagine;
- $R_{15}$ is lysine; and,
- $R_{16}$ is cysteine or penicillamine.

16. The method of claim 15 wherein said conformationally restricted peptide consists of SEQ ID NO:4.

17. The method of claim 13 wherein said individual is about to undergo, is undergoing and/or has undergone a transplantation procedure selected from the group consisting of bone marrow transplants, liver transplants, heart transplants, kidney transplants, lung transplants, islets transplants, cornea transplants and skin grafts.

18. The method of claim 13 wherein said individual is suspected of suffering from or susceptible to graft versus host disease.

* * * * *